United States Patent [19]
Tsuchida et al.

[11] 3,962,034
[45] June 8, 1976

[54] METHOD FOR PRODUCING S-ADENOSYLMETHIONINE OR METHYLTHIOADENOSINE BY YEAST

[75] Inventors: Takayasu Tsuchida, Kawasaki; Fumihiro Yoshinaga, Fujisawa; Shinji Okumura, Tokyo, all of Japan

[73] Assignee: Ajinomoto Co., Inc., Tokyo, Japan

[22] Filed: Nov. 25, 1974

[21] Appl. No.: 527,071

[30] Foreign Application Priority Data
Nov. 27, 1973 Japan............................. 48-13309
Nov. 27, 1973 Japan............................. 48-13310

[52] U.S. Cl................................. 195/28 N; 195/29
[51] Int. Cl.² ....................................... C12D 13/06
[58] Field of Search........................... 195/29, 28 N

[56] References Cited
UNITED STATES PATENTS
3,563,857  2/1971  Oki et al. ............................. 195/49
3,619,368  11/1971  Woldendorp ......................... 195/30

OTHER PUBLICATIONS
Agr. Biol. Chem. vol. 3, No. 1 pp. 73–76 and 664–670 (1967).
J. Biol. Chem. vol. 233 pp. 1037–1057 (1958).

Primary Examiner—Alvin E. Tanenholtz
Attorney, Agent, or Firm—Cooper, Dunham, Clark, Griffin & Moran

[57] ABSTRACT

S-adenosylmethionine and methylthioadenosine are produced in the culture medium of yeast grown in a media containing L-methionine.

9 Claims, No Drawings

METHOD FOR PRODUCING S-ADENOSYLMETHIONINE OR METHYLTHIOADENOSINE BY YEAST

This invention relates to a method for producing N-adenozylmethionine(S-5′-desoxyadenosine-5′-yl)methionine) or methylthioadenosine (1-adenyl-5-methylthioribose). S-Adenosylmethionine and methylthioadenosine will be referred to simply as "SAM" and "MTA", respectively, hereinafter.

SAM is known as an active-methionine, and has an anti-fatty liver activity. It is also known that small amount of SAM is contained in a culture medium and/or cells of baker's yeast, Saccharomyces cerevisiae ("Amino Acid" No. 4, p.p. 95–98, 1961 (Japan) and Japanese unexamined patent publication No. 44491/1973) and that small amounts of both S-adenosylmethionine and methylthioadenosine are contained in cells of Torulopsis utilis (J.B.C., 229, 1037 (1957)), when the microorganisms are cultured in the presence of small amounts of methionine.

MTA is known as vitamine $L_2$ and promotes secretion of milk, and has been produced from SAM by hydrolysis (Arch. Biochem. Biophys. 75, 291 (1958); J. Biol. Chem. 233, 631 (1958)).

It has been now found that surprisingly high amounts of SAM and/or MTA are accumulated in the culture broth and/or in cells of various yeasts, when the yeasts are cultured in otherwise conventional medium containing as much as 0.5 to 2.0 g/dl L-methionine with maintaining a pH of the medium at 2 to 5 and preferably 3 to 5.

It is known that L-methionine is necessary for the accumulaton of SAM by baker's yeast, but it is surprising that extremely large amounts of SAM together with extremely large amounts of MTA are produced, when the same yeast of genus Saccharomyces is cultured by the specific culture conditions of pH and the amount of methionine in the medium.

Yeasts which produce SAM or MTA, found so far, belong to genus Candida, Pichia, Rhodotorula, Cryptococcus, Hansenula, Trycosporon, Kloeclera, Torulopsis, Hanseniaspora, Sporoboromyces, Lipomyces or Debaryomyces. Most of the yeasts produce SAM and MTA at the same time in the culture broth and in the cells.

The culture media of this invention are conventional except for containing 0.5 to 2.0 g/dl L-methionine. The media also contain carbon source, nitrogen source, and inorganic ions. For a certain yeast, minor organic nutrients such as vitamines or amino acids are necessary for or promote the growth.

Carbohydrates (such as glucose, sucrose, maltose, fructose, starch, or cellulose), alcohols (such as methanol, ethanol, propanol, glycerol, sorbitol, or xylulose), organic acids (such as acetic acid, propionic acid, butylic acid, glyceric acid, higher fatty acid, fumaric acid, or benzoic acid), esters, alkanes or aldehydes, or raw materials which contain those carbon source (such as starch hydrolyzate, molasses, soy whey, fruit juice, waste water of fish processing, fermentation processing water, or pulp processing water) are used as the carbon source.

Suitable nitrogen sources are ammonium salts, ammonia water, gaseous ammonia, urea, nitrate salts, and amino acid.

Inorganic salts are conventional such as phosphate, sulfate, and salts of potassium, magnesium, sodium, iron, manganese and calcium.

Cultivation is carried out maintaining pH to 2 to 5, preferably 3 to 5 with alkali or acid, and temperature to 25° to 40°C. Normally, the fermentation period is from 2 to 10 days, although some variation is possible, to accumulate SAM or MTA.

SAM accumulated in culture broth or cells can be recovered by using an ion exchange resin or other known methods. Also cells themselves which contain S-adenosylmethionine are recovered as the SAM.

MTA accumulated in culture broth or cells can be recovered also by using an ion exchange resin or other known method. The MTA in the cells is recovered in the form contained in the cells, or from the homogenate of the cells by conventional methods.

Especially, cells containing SAM and/or MTA useful as an additive of feed. It is also possible to use the culture broth, as it is or after processed, as a feed additive.

EXAMPLE 1

An aqueous culture medium was prepared to contain, per deciliter, 5 g glucose, the amount of methionine shown in Tables 1 to 4, 3 ml soyprotein hydrolyzate, 0.5 g $KH_2PO_4$, and 0.04 g $MgSO_4 \cdot 7H_2O$, and adjusted to each pH shown in Table 1 to 4. 20 ML batches of the aqueous culture medium were placed in 500 ml flasks, heated with steam, and inoculated with each Saccharomyces marxianus IFO 0272 and Hansenula polymorpha IFO 0799. Cultivation was carried out at 31.5°C with shaking for 72 hours. A pH of medium was adjusted to the level shown in Tables 1 to 4 with ammonia water.

SAM and MTA in the culture broth and in the homogenate of the cells were determined by cutting the spots of SAM and MTA on paper chromatography and measuring optical densities each at 260 m$\mu$. The results are shown in Tables 1 to 4.

EXAMPLE 2

Candida lipolytica IFO 0746 was cultured by the same manner as shown in Example 1. A pH of medium was maintained at a pH of 4 with ammonia water.

The amounts of SAM and MTA as shown in Table 5 were accumulated in the culture broth.

EXAMPLE 3

L-Methionine in the medium shown in Example 1 was used in the amount of 1 g/dl, and in which Candida lipolytica IFO 0746 was cultured by the same manner as shown in Example 1. A pH of medium was adjusted at the level shown in Table 6 with ammonia water.

The amounts of SAM and MTA shown in Table 6 was accumulated in the culture broth.

EXAMPLE 4

Candida tropicalis IFO 0618 was cultured by the same manner as shown in Example 2, and accumulated the amounts of MTA and SAM in the culture broth as shown in Table 7.

EXAMPLE 5

Candida tropicalis IFO 0618 was cultured by the same manner as shown in Example 3. The amounts of MTA and SAM were accumulated in the culture broth as shown in Table 8.

EXAMPLE 6

The yeasts as shown in Table 9 were cultured in the medium of Example 1 containing 1 g/dl L-methionine by maintaining a pH of medium at 4.0 with ammonia water.

SAM and MTA were accumulated in the culture broth and in the cells as shown in Table 9.

EXAMPLE 7

Candida lipolytica IFO 0746 was cultured in a seed culture medium containing, per deciliter, 3 g glucose, 0.1 g $KH_2PO_4$, 0.04 g $MgSO_4.7H_2O$, 0.2 g yeast extract, 3 ml soyprotein-hydrolyzate, (of pH 4.0) at 31.5°C for 24 hours.

An aqueous culture medium was prepared to contain, per deciliter, 0.4 g ammonium acetate, 0.4 g potassium acetate, 0.1 g $KH_2PO_4$, 0.04 g $MgSO_4.7H_2O$, 3 ml soyprotein-hydrolyzate, 1 g L-methionine, adjusted to pH 4.0, and 300 ml of the medium was placed in 1 liter fermenter.

The seed culture broth as shown above (15 ml) was transferred to the 1 liter fermenter. The medium was maintained at 31.5°C, and at pH 3.5 to 4.5 by feeding 70% acetic acid and gaseous ammonia, agitated and aerated.

After 48 hours cultivation, 205 mg/dl and 85 mg/g-dry cell SAM were found in the culture broth and in the cells, respectively.

EXAMPLE 8

In the same manner as shown in Example 7, Saccharomyces merxianus IFO 0272 was cultured for 48 hours, and 120 mg/dl and 75 mg/g-dry cell MTA were found in the culture broth and in the cells, respectively.

EXAMPLE 9

The seed culture broth as shown in Example 7 (15 ml) was transferred to 300 ml of an aqueous culture medium placed in 1 liter fermenter and containing, per deciliter, 0.5 ml methanol, 0.1 g $KH_2PO_4$, 0.04 g $MgSO_4.7H_2O$, 3 ml soyprotein-hydrolyzate, and 1 g L-methionine.

Cultivation was carried out aerobically by adjusting to 31.5°C, and to pH 3.5–4.5 with gaseous ammonia. The concentration of methanol in the medium was maintained at 0.2–0.5 g/dl by feeding methanol.

After 72 hours cultivation, 60 mg/dl and 80 mg/g-dry cell SAM were accumulated in the culture broth and in the cells, respectively.

EXAMPLE 10

In the same manner as shown in Example 9, Candida tropicalis IFO 0618 was cultured for 72 hours, and 78 mg/dl and 130 mg/g-dry cell MTA were found in the culture broth and in the cells, respectively.

Example 11

In the same manner as shown in Example 9, 1 g/dl ethanol was used as the carbon source in place of methanol, and 15 ml of seed culture broth of Hansenura polymorpha IFO 0799 prepared by the same method as shown in Example 7 was inoculated in the medium.

Cultivation was carried out by the same manner as shown in Example 9 for 48 hours.

The results are shown in Table 10.

EXAMPLE 12

Twenty ml aliquat of an aqueous culture medium containing, per deciliter, 5 g n-hexane, 1 g L-methionine, 0.1 g $KH_2PO_4$, 0.04g $MgSO_4.7H_2O$, and 0.2 g yeast extract was placed in 500 ml flask, and inoculated with 20 ml of seed culture broth of Candida lipolytica IFO 0746 prepared by the same manner as shown in Example 7. Cultivation was carried out at 31.5°C for 48 hours with adjusting pH at 4.0 with gaseous ammonia. The results are shown in Table 11.

EXAMPLE 13

An aqueous culture medium was prepared to contain, per deciliter, 10 ml soy-whey (containing 53.4% sugars and 7.1% organic acids); 1 g L-methionine, 0.1 g $KH_2PO_4$, 0.04 g $MgSO_4. 7H_2O$, and 1 ml soyprotein-hydrolyzate, adjusted to pH 4.0, and 20 ml alquot of the medium was placed in 500 ml flask.

Candida lipolytica IFO 0746 was inoculated in the medium and cultured at 31.5°C for 48 hours with shaking. A pH of medium was maintained at 4.0 with gaseous ammonia. The results are shown in Table 12.

EXAMPLE 14

Two liter of culture broth of Pichia mogii IFO 0607 were prepared by the same manner as in Example 6. The resulted broth contained 190 mg/dl SAM in supernatant, and 1.3 g dry cells/dl containing 80 mg/g-dry cell S-adenosyl methionine.

The supernatant was passed through a cation exchange resin column and SAM was absorbed on theresin, which was subsequently eluted with 0.1–3M $H_2SO_4$. The eluate was added with Reineck's salts. The precipitate formed was collected and dissolved again in water. Reineck's salts were removed with methylethylketone, and thereafter 2.3 g SAM crystals were obtained.

The cells (250 g) of Pichia mogii IFO 0607 were extracted with 1.5 liter of 1.5N perchloric acid. The extract was passed through a cation exchange resin. The absorbed SAM was eluted with 0.1M–3M $H_2SO_4$ and precipitated with Reineck's salts. SAM was crystallized after removing Reineck's salts. It weighed 14.8 g.

EXAMPLE 15

Two liter of culture broth of Candida pseudotropicalis IFO 1065 were prepared by the same manner as in Example 6. The broth contained 150 mg/dl MTA, and 1.0 g/dl cells containing 85 mg/g-dry cell MTA.

The supernatant was passed through a cation exchange resin, and MTA was absorbed on the resin. MTA was eluted with 0.1M $H_2SO_4$, and crystallized. It weighed 1.4 g.

EXAMPLE 16

Candida lipolytica IFO 0746 was cultured in 70 liter fermenter containing 30 liter of the medium shown in Example 1. Cultivation was carried out aerobically at ph 4.0, and at 30°C. After 48 hours cultivation, the cells contained 61 mg/g-dry cell SAM and 42 mg/g-dry cell MTA.

A portion of the culture broth (25 liter) was centrifuged to separate cells and the cells were dried at 105°C. They weighed 26.5 g.

A feed was prepared to contain 75% rice powder, 10% fish protein, 10% butter and 2.5% dried baker's yeast on the market. 20 Mice were cultured by feeding each 25 g the feed a day in a room controlled at 23°C.

When the mice grew to 80 g, 10 mice were fed with the feed further containing 50 mg/100 g ethionine. After 80 days, 3 out of the 10 mice were found to have fatty liver, while the remaining 7 mice had normal liver. On the other hand, the remaining 10 mice were fed with the feed further containing both 50 mg/100 g ethionine and 5 g/100 g Candida cells separated and dried above. After 80 days, all mice were found to have normal liver.

The remaining portion of the culture broth, when used as a feed additive in the same manner after evaporated almost to dryness, gave similar results to the separated and dried Candida cells.

Table 1

SAM Accumulated in the Culture Broth

| Methionine added (g/dl) | Micro-organism | pH 1 | 2 | 3 | 4 | 5 | 6 | 7 | 8 |
|---|---|---|---|---|---|---|---|---|---|
| | | | | | (mg/dl) | | | | |
| 0 | IFO 0272 | 0 | 0 | 0 | 0 | 0 | 0 | 0 | 0 |
| | IFO 0799 | 0 | 0 | 0 | 0 | 0 | 0 | 0 | 0 |
| 0.2 | IFO 0272 | 0 | 0 | 2 | 1 | 1 | 1 | 0 | 0 |
| | IFO 0799 | 0 | 0 | 2 | 1 | 1 | 1 | 0 | 0 |
| 0.5 | IFO 0272 | 0 | 70 | 20 | 81 | 78 | 25 | 10 | 0 |
| | IFO 0799 | 0 | 65 | 78 | 79 | 70 | 30 | 8 | 0 |
| 1.0 | IFO 0272 | 0 | 85 | 90 | 108 | 105 | 43 | 9 | 0 |
| | IFO 0799 | 0 | 90 | 85 | 100 | 100 | 40 | 6 | 0 |
| 1.5 | IFO 0272 | 0 | 80 | 195 | 130 | 180 | 53 | 8 | 0 |
| | IFO 0799 | 0 | 80 | 190 | 185 | 180 | 55 | 10 | 0 |
| 2.0 | IFO 0272 | 0 | 80 | 200 | 210 | 190 | 48 | 7 | 0 |
| | IFO 0799 | 0 | 95 | 205 | 200 | 200 | 40 | 8 | 0 |
| 2.5 | IFO 0272 | 0 | 10 | 10 | 30 | 20 | 5 | 1 | 0 |
| | IFO 0799 | 0 | 20 | 40 | 40 | 45 | 3 | 1 | 0 |

Table 2

MTA Accumulated in the Culture Broth

| Methionine added (g/dl) | Micro-organism | pH 1 | 2 | 3 | 4 | 5 | 6 | 7 | 8 |
|---|---|---|---|---|---|---|---|---|---|
| | | | | | (mg/dl) | | | | |
| 0 | IFO 0272 | 0 | 0 | 0 | 0 | 0 | 0 | 0 | 0 |
| | IFO 0799 | 0 | 0 | 0 | 0 | 0 | 0 | 0 | 0 |
| 0.2 | IFO 0272 | 0 | 0 | 2 | 2 | 1 | 1 | 0 | 0 |
| | IFO 0799 | 0 | 0 | 2 | 2 | 1 | 0 | 0 | 0 |
| 0.5 | IFO 0272 | 0 | 40 | 70 | 90 | 89 | 20 | 7 | 3 |
| | IFO 0799 | 0 | 50 | 80 | 95 | 90 | 23 | 8 | 5 |
| 1.0 | IFO 0272 | 0 | 70 | 95 | 110 | 100 | 38 | 10 | 7 |
| | IFO 0799 | 0 | 80 | 98 | 108 | 101 | 40 | 12 | 8 |
| 1.5 | IFO 0272 | 0 | 80 | 210 | 198 | 195 | 42 | 10 | 10 |
| | IFO 0799 | 0 | 80 | 200 | 190 | 190 | 48 | 11 | 10 |
| 2.0 | IFO 0272 | 0 | 90 | 210 | 200 | 200 | 46 | 12 | 12 |
| | IFO 0799 | 0 | 95 | 205 | 210 | 189 | 43 | 14 | 11 |
| 2.5 | IFO 0272 | 0 | 10 | 50 | 70 | 60 | 10 | 3 | 0 |
| | IFO 0799 | 0 | 10 | 50 | 80 | 65 | 15 | 2 | 1 |

Table 3

SAM Accumulated in the Cells

| Methionine added (g/dl) | Micro-organism | pH 1 | 2 | 3 | 4 | 5 | 6 | 7 | 8 |
|---|---|---|---|---|---|---|---|---|---|
| | | | | | (mg/g-dry cell) | | | | |
| 0 | IFO 0272 | 0 | 0 | 0 | 0 | 0 | 0 | 0 | 0 |
| | IFO 0799 | 0 | 0 | 0 | 0 | 0 | 0 | 0 | 0 |
| 0.2 | IFO 0272 | 0 | 2 | 2 | 1 | 1 | 1 | 0 | 0 |
| | IFO 0799 | 0 | 1 | 2 | 1 | 1 | 1 | 0 | 0 |
| 0.5 | IFO 0272 | 0 | 38 | 40 | 35 | 37 | 10 | 7 | 1 |
| | IFO 0799 | 0 | 33 | 30 | 38 | 30 | 15 | 5 | 0 |
| 1.0 | IFO 0272 | 0 | 98 | 100 | 103 | 98 | 30 | 9 | 1 |
| | IFO 0799 | 0 | 95 | 120 | 105 | 95 | 40 | 9 | 0 |
| 1.5 | IFO 0272 | 0 | 170 | 190 | 195 | 205 | 55 | 9 | 1 |
| | IFO 0799 | 0 | 175 | 195 | 200 | 210 | 60 | 11 | 2 |
| 2.0 | IFO 0272 | 0 | 173 | 205 | 210 | 210 | 50 | 10 | 1 |
| | IFO 0799 | 0 | 181 | 203 | 215 | 210 | 65 | 5 | 0 |
| 2.5 | IFO 0272 | 0 | 70 | 68 | 50 | 63 | 10 | 1 | 0 |
| | IFO 0799 | 0 | 60 | 69 | 55 | 70 | 5 | 0 | 0 |

Table 4

MTA Accumulated in the Cells

| Methionine added (g/dl) | Micro-organism | pH 1 | 2 | 3 | 4 | 5 | 6 | 7 | 8 |
|---|---|---|---|---|---|---|---|---|---|
| | | | | | (mg/g-dry cell) | | | | |
| 0 | IFO 0272 | 0 | 0 | 0 | 0 | 0 | 0 | 0 | 0 |
| | IFO 0799 | 0 | 0 | 0 | 0 | 0 | 0 | 0 | 0 |
| 0.2 | IFO 0272 | 0 | 1 | 1 | 1 | 1 | 0 | 0 | 0 |
| | IFO 0799 | 0 | 0 | 1 | 1 | 1 | 0 | 0 | 0 |
| 0.5 | IFO 0272 | 0 | 35 | 30 | 35 | 36 | 9 | 5 | 1 |
| | IFO 0799 | 0 | 36 | 36 | 38 | 35 | 10 | 3 | 0 |
| 1.0 | IFO 0272 | 0 | 85 | 106 | 105 | 98 | 20 | 3 | 1 |
| | IFO 0799 | 0 | 90 | 110 | 110 | 96 | 15 | 5 | 0 |
| 1.5 | IFO 0272 | 0 | 120 | 120 | 128 | 129 | 30 | 3 | 1 |
| | IFO 0799 | 0 | 115 | 135 | 130 | 130 | 38 | 4 | 0 |
| 2.0 | IFO 0272 | 0 | 118 | 138 | 140 | 132 | 48 | 3 | 0 |
| | IFO 0799 | 0 | 119 | 142 | 145 | 140 | 45 | 2 | 1 |
| 2.5 | IFO 0272 | 0 | 40 | 52 | 58 | 53 | 10 | 1 | 0 |
| | IFO 0799 | 0 | 28 | 58 | 53 | 58 | 5 | 0 | 0 |

Table 5

| Methionine added (g/dl) | SAM (mg/dl) | MTA (mg/dl) |
|---|---|---|
| 0.0 | 0 | 0 |
| 0.2 | 45 | 38 |
| 0.5 | 100 | 96 |
| 1.0 | 110 | 100 |
| 1.5 | 180 | 175 |
| 2.0 | 130 | 120 |
| 2.5 | 30 | 5 |

Table 6

| pH | SAM (mg/dl) | MTA (mg/dl) |
|---|---|---|
| 1 | 0 | 0 |
| 2 | 80 | 60 |
| 3 | 200 | 180 |
| 4 | 190 | 185 |

Table 6-continued

| pH | SAM (mg/dl) | MTA (mg/dl) |
|---|---|---|
| 5 | 195 | 186 |
| 6 | 105 | 100 |
| 7 | 90 | 70 |
| 8 | 35 | 20 |

Table 7

| Methionine added (g/dl) | MTA (mg/dl) | SAM (mg/dl) |
|---|---|---|
| 0.0 | 0 | 0 |
| 0.2 | 65 | 70 |
| 0.5 | 110 | 130 |
| 1.0 | 108 | 125 |
| 1.5 | 108 | 130 |
| 2.0 | 60 | 70 |
| 2.5 | 65 | 68 |

Table 8

| pH | MTA (mg/dl) | SAM (mg/dl) |
|---|---|---|
| 1 | 0 | 0 |
| 2 | 65 | 67 |
| 3 | 110 | 120 |
| 4 | 108 | 168 |
| 5 | 108 | 160 |
| 6 | 60 | 65 |
| 7 | 65 | 60 |
| 8 | 30 | 40 |

Table 9

| | SAM | | MTA | |
|---|---|---|---|---|
| | in broth (mg/dl) | in cells (mg/g-dry cell) | in broth (mg/dl) | in cells (mg/g-dry cell) |
| Pichia mogii IFO 0607 | 190 | 80 | 90 | 40 |
| Rhodotorula rubra IFO 0607 | 110 | 50 | 55 | 32 |
| Torulopsis anomala IFO 1228 | 80 | 45 | 40 | 20 |
| Trichosporon fermentans IFO 1199 | 60 | 30 | 30 | 10 |
| Lipomyces starkeii IFO 0678 | 88 | 35 | 20 | 10 |
| Debaryomyces hansenii IFO 0033 | 90 | 42 | 30 | 10 |
| Sporoboromyces roseus IFO 1037 | 85 | 38 | 35 | 15 |
| Cryptococcus terreus IFO 0727 | 73 | 30 | 38 | 14 |
| Kloeckera africana IFO 1340 | 85 | 35 | 35 | 10 |
| Hanseniaspora valbyensis IFO 0670 | 80 | 35 | 40 | 12 |

Table 10

| | In broth (mg/dl) | In cells (mg/g-dry cells) |
|---|---|---|
| SAM | 130 | 78 |
| MTA | 130 | 78 |

Table 11

| | In broth (mg/dl) | In cells (mg/g-dry cells) |
|---|---|---|
| SAM | 90 | 50 |
| MTA | 84 | 43 |

Table 12

| | In broth (mg/dl) | In cells (mg/g-dry cells) |
|---|---|---|
| SAM | 95 | 48 |
| MTA | 82 | 45 |

What is claimed is:

1. In a method for producing S-adenosylmethionine and methylthioadenosine which comprises culturing a yeast selected from the group consisting of members of the genus Saccharomyces, Candida, Pichia, Rhodotorula, Torulopsis, Trichosporon Lipomyces, Debaryomyces, Sporoboromyces, Cryptococcus, Kloechera Hansenula and Hanseniaspora in an aqueous culture medium and recovering S-adenosylmethionine and methylthioadenosine therefrom, the improvement which comprises including from 0.5 to 2.0 g/dl of L-methionine in the culture medium, continuing the culturing at a pH of from 2 to 5 until the concentration of S-adenosylmethionine which accumulates in the culture medium is at least 60 mg/dl in the broth and 30 mg/g in the cells, based on the weight of dry cells, and the concentration of methylthioadenosine which accumulates in the culture medium is at least 20 mg/dl in the broth and 10 mg/g in the cells, based on the weight of dry cells and recovering the accumulated S-adenosylmethionine and methylthioadenosine from the culture medium.

2. A method as set forth in claim 1, wherein said yeast belongs to genus Saccharomyces.

3. A method as set forth in claim 1, wherein said yeast belongs to genus Candida.

4. A method as set forth in claim 1, wherein said yeast belongs to genus Pichia.

5. A method as set forth in claim 1, wherein said yeast belongs to genus Hansenula.

6. A method as set forth in claim 1, wherein said aqueous culture medium contains ethanol or methanol as the carbon source.

7. A method as set forth in claim 1, wherein said aqueous culture medium contains acetic acid as the carbon source.

8. A method as set forth in claim 1, wherein said aqueous culture medium contains ethanol as the carbon source.

9. A method as set forth in claim 1, wherein said aqueous culture medium contains carbohydrate as the carbon source.

* * * * *